United States Patent [19]

Herkes

[11] 4,279,815

[45] Jul. 21, 1981

[54] PRODUCTION OF HIGH-QUALITY AROMATIC AMINO AZO COMPOUNDS BY THE REARRANGEMENT OF 1,3-DIARYL TRIAZENES

[76] Inventor: Frank E. Herkes, 2530 Dartmouth Woods Rd., Wilmington, Del. 19810

[21] Appl. No.: 2,010

[22] Filed: Jan. 9, 1979

[51] Int. Cl.³ ................. C07C 107/06; C07C 115/00; C09B 27/00
[52] U.S. Cl. .................................. 260/205; 260/140; 423/390
[58] Field of Search ........................ 260/140, 205, 578

[56] References Cited

U.S. PATENT DOCUMENTS

| | | | |
|---|---|---|---|
| 1,977,266 | 10/1934 | Dahlen | 260/205 |
| 2,133,037 | 10/1938 | Moyer | 260/140 |
| 2,538,431 | 1/1951 | Shulman | 260/205 |
| 2,809,964 | 10/1957 | Baggenstoss et al. | 260/205 |
| 2,894,942 | 7/1959 | Hydro et al. | 260/205 |
| 4,018,751 | 4/1977 | Trecek | 260/205 |
| 4,020,052 | 4/1977 | Detrick | 260/140 X |

FOREIGN PATENT DOCUMENTS

| | | | |
|---|---|---|---|
| 580083 | 7/1959 | Canada | 260/205 |
| 1430366 | 3/1976 | United Kingdom | 260/205 |

*Primary Examiner*—Floyd D. Higel

[57] ABSTRACT

A 1,3-diaryl triazene, in a solution obtained by the diazotization-coupling of a primary aromatic monoamine with a gas containing NO and $NO_2$, which solution contains the monoamine and up to about 30 percent by weight of the triazene, based on the weight of the solution, is contacted with 0.4–2.0 percent of a strong acid, preferably nitric acid (based on the weight of the triazene-containing solution), at 50°–120° C. The triazene rearranges to an aromatic amino azo compound in a high para/ortho isomer ratio with minimum formation of binuclear by-products.

10 Claims, No Drawings

PRODUCTION OF HIGH-QUALITY AROMATIC AMINO AZO COMPOUNDS BY THE REARRANGEMENT OF 1,3-DIARYL TRIAZENES

BACKGROUND OF THE INVENTION

1. Field of the Invention

The present invention relates to a method of producing aromatic amino azo compounds, e.g., p-aminoazobenzene, by the rearrangement of 1,3-diaryl triazenes, e.g., 1,3-diphenyltriazine.

2. Description of the Prior Art

Aromatic amino azo compounds are useful as solvent dyes and as intermediates in the preparation of aromatic diamines, which, in turn, are used in the preparation of polymers, antioxidants, etc.

U.S. Pat. No. 1,977,266 describes the reaction of sodium nitrite with solid aniline hydrochloride formed into a paste with water to form diazoaminobenzene by diazotization-coupling, followed by raising the temperature of the reaction mixture to slowly rearrange the diazoamino compound to 4-aminoazobenzene, the latter being obtained in the form of its hydrochloric acid salt. The rearrangement is carried out over a period of several hours at temperatures in the range of 20° C. to 40° C.

According to the process of U.S. Pat. No. 2,538,431, the rearrangement of the diazoamino to the amino azo compound is carried out in the same stage as the diazotization-coupling reaction in an alcohol medium. The diazotizing agent, i.e., a nitrite or nitrous acid, is admixed with a solution of the amine in hydrochloric acid and a restricted amount of an alcohol. A temperature of 10° C. to 40° C. and a reaction time of 15 to 45 minutes are critical features.

U.S. Pat. No. 2,894,942 describes the formation of aromatic amino azo compounds by adding an inorganic nitrite to a mixture of an excess of a primary aryl monoamine, a mineral acid, and a Friedel-Crafts catalyst while the temperature is 0°–50° C. (20°–30° C. preferred) whereby a portion of the amine is diazotized and the diazonium salt couples with unreacted amine to form the diazoamino aryl compound; and thereafter heating up to about 40°–75° C. (45°–55° C. preferred) for a period of about from one-half to three hours whereby the diazoamino aryl compound rearranges to the amino azo compound under the combined influence of the Friedel-Crafts catalyst and heat. Temperatures above 75° C. are disclosed as accelerating side-reactions. Without the Friedel-Crafts catalyst, the rearrangement is disclosed as requiring over six hours to complete. The same process is described in Canadian Pat. No. 580,083, except that the mineral acid is used in excess, and the Friedel-Crafts catalyst is omitted.

British Pat. No. 1,430,366 also describes rearranging the diazoaminobenzene in a reaction mixture obtained by reacting aniline with nitrous acid generated by mixing an alkali metal nitrite with an aqueous mineral acid. For the rearrangement, the aniline solution of the diazoaminobenzene is treated with aniline hydrochloride at 20° to 100° C. for several hours.

In the continuous process described in U.S. Pat. No. 4,018,751, wherein reactant streams comprising (a) an aromatic primary amine, mineral acid, and water and (b) aqueous metal nitrite solution are passed through a tubular reactor, and a p-aminoazo compound is recovered from the exiting stream, the reactor temperature is 40° to 100° C. and the residence time therein less than ten minutes.

In all of the above-discussed prior art, the diazotization of the aromatic amine to produce the diazoamino compound needed for the rearrangement is carried out in the conventional manner with an inorganic nitrite and an acid, or with nitrous acid generated therefrom. Such processes, when considered in terms of large-scale operations, suffer from the disadvantage that the salt, e.g., sodium chloride, produced as a by-product of the diazotization reaction needs to be separated and disposed of. This disadvantage recently has been overcome with the discovery of a process for the diazotization-coupling of primary aromatic monoamines by means of a nitrogen oxide-containing gas mixture derived from the oxidation of ammonia. This new process is described in U.S. Pat. No. 4,020,052, issued Apr. 26, 1977, the disclosure of which is incorporated herein by reference. One desirable feature of the process is that it produces no salt by-products requiring troublesome salt separation procedures. Another is that, unlike the product obtained in the prior art processes, a triazene-containing reaction product in the form of a homogeneous liquid can be obtained, an advantage if the liquid is to be used per se for a subsequent triazene reaction.

When diazoaminobenzene, for example, is synthesized by the diazotization of aniline with a nitrogen oxide-containing gas, the reaction product obtained is comprised of 1,3-diphenyltriazine dissolved in aniline, this solution possibly also containing, depending on the composition of the nitrogen oxides used and other reaction conditions, small amounts of aminoazobenzenes, aminobiphenyls, other nitrogen-containing polynuclear compounds, water, and/or nitric acid. During the rearrangement of the 1,3-diphenyltriazine in this solution, side-reactions leading to the formation of polynuclear (chiefly binuclear) by-products such as aminobiphenyls may occur. Also, yield losses to the undesired o-aminoazobenzene isomer may result.

The prior art has not addressed itself to the problem of the formation of polynuclear by-products in the rearrangement of 1,3-diaryl triazenes in solutions obtained by treating primary aromatic amines with nitrogen oxide-containing gases, or to the question of optimizing the production of the p-aminoazobenzene isomer in this system. These problems must be recognized and solved, however, if the aminoazobenzene process is to achieve its potential. The minimizing of the polynuclear by-product content is important on two counts. First, polynuclear by-products per se represent a yield loss and generally are reflective of additional losses due to tar formation. Secondly, and most importantly, 4-aminobiphenyl, a possible binuclear by-product of the rearrangement reaction, has been recognized as having carcinogenic properties. Accordingly, it is important to suppress the formation of binuclear by-products as much as possible, a practical level for total binuclear by-products being below 2%.

"Binuclear by-products," as the term is used herein, consist predominantly of 2-, 3-, and 4-aminobiphenyls and diphenylamine, and trace amounts of other similar binuclear compounds having nitrogen-containing substituents.

A process is needed for rearranging a 1,3-diaryl triazene in a solution obtained by the diazotization-coupling of a primary aromatic monoamine by means of a nitrogen oxide-containing gas mixture, which process minimizes the formation of binuclear by-products and preferably also maximizes the para/ortho isomer ratio of the aromatic amino azo compound.

SUMMARY OF THE INVENTION

The present invention provides a method of preparing a carbocyclic aromatic amino azo compound, e.g., p-aminoazobenzene, comprising contacting a strong acid, preferably nitric acid, at a temperature in the range of about from 50° to 120° C., preferably up to about 90° C., with a solution obtained by the treatment of an excess of a primary carbocyclic aromatic monoamine, e.g., aniline, with a gas containing nitric oxide and nitrogen dioxide to effect diazotization-coupling, this solution being substantially homogeneous at said temperature and containing primary carbocyclic aromatic monoamine and up to about 30, preferably about from 15 to 25, percent by weight of a dissolved 1,3-diaryl triazene based on the weight of the solution, and the weight of the strong acid being about from 0.4 to 2.0 percent of the weight of the triazene-containing solution contacted therewith. A rearrangement product solution is obtained containing an aromatic amino azo compound in a para/ortho isomer ratio of at least about 7/1 and binuclear by-products amounting to no more than about two percent by weight, based on the total weight of the solution.

Preferably, the monoamine is liquid under the diazotization-coupling, as well as the rearrangement, conditions and serves as a solvent for the triazene and the amino azo compound. In such a case, the solution with which the strong acid is contacted is a solution of the triazene in the monoamine (that which is unconsumed in the diazotization-coupling reaction, with or without added monoamine).

In a preferred embodiment of the invention, the solution of a 1,3-diaryl triazene in a primary carbocyclic aromatic monoamine is the reaction product obtained by treating an excess of a primary carbocyclic aromatic monoamine with a gas mixture derived from the oxidation of ammonia, most preferably with a mixture comprising nitric oxide, nitrogen dioxide, an inert diluent such as nitrogen, and water vapor. This substantially homogeneous reaction product, described more fully in the aforementioned U.S. Pat. No. 4,020,052, may contain small amounts of nitric acid and, accordingly, to maintain a consistency between the diazotization-coupling and rearrangement systems, it is preferred that the strong acid which is contacted with the triazene-containing solution be nitric acid.

DETAILED DESCRIPTION

In the method of this invention, a 1,3-diaryl triazene, present in a solution in which it has been formed by the diazotization-coupling of a primary carbocyclic aromatic monoamine by means of a nitrogen oxide-containing gas, is rearranged to an aromatic amino azo compound. The triazene can be one that has no ring substituents, e.g., 1,3-diphenyltriazene; or ring substituents which are inert toward the strong acid, as well as to the nitrogen oxides used in the triazene-forming reaction. Inertness toward nitrogen oxides is required because any ring substituents in the triazene to be rearranged will have been present in the primary carbocyclic aromatic monoamine from which it is derived and will have had to survive exposure to the diazotization-coupling conditions. Thus, the triazene and its monoamine precursor can have, for example, one or more substituents selected from alkyl, aryl, halo, haloalkyl, alkoxy, and nitro substituents; preferred alkyl, haloalkyl, and alkoxy substituents having 1 to 4 carbon atoms. Substitution can be present in any position with respect to the diazoamino group in the triazene, and to the amino group in its monoamine precursor, provided that the ortho- and/or the para-positions are open. From the standpoint of present technical importance, aromatic amino azo compounds in which the amino and azo groups are in the para-position to each other are preferred, and for this reason preferred triazenes have unsubstituted para-positions. In addition to 1,3-diphenyltriazene (precursor: aniline), other triazenes which can be used include 1,3-ditolyltriazene (precursor: toluidine, preferably ortho or meta), 1,3-dixylyltriazene (precursor: dimethylaniline, preferably 2,3-, 2,5-, 2,6-, or 3,5-), and 1,3-bis(halophenyl)- or bis(nitrophenyl)triazene (precursor: halo- or nitroaniline, preferably ortho or meta).

The triazene is rearranged in a solution obtained by treating an excess of a primary carbocyclic aromatic monoamine with a nitrogen oxide-containing gas to effect diazotization-coupling. For reasons explained in the aforementioned U.S. Pat. No. 4,020,052, the diazotizing agent preferably is a gas mixture derived from the oxidation of ammonia. One advantage of the nitrogen oxide system is that a homogeneous solution is obtained, which can be used directly for the rearrangement. In this solution, the triazene is dissolved in the precursor monoamine, or in a solution of a monoamine. As is disclosed in the aforementioned U.S. Pat. No. 4,020,052, neat, dissolved, or diluted monoamine can be used in the diazotization-coupling reaction, but preferably the monoamine is a neat liquid and sufficiently unconsumed in the reaction so as to act as a solvent for the triazene formed, giving a liquid reaction product that is homogeneous in the range of temperatures used for the rearrangement. Homogeneity, or the absence of multiple phases, is beneficial in that it permits the use of less acid catalyst in the rearrangement and makes it easier to achieve uniformity of conditions throughout the reaction solution.

The triazene-containing solution used as the starting material in the preferred rearrangement method of this invention, i.e., the solution obtained by the diazotization-coupling method described in U.S. Pat. No. 4,020,052, contains the triazene and unconsumed monoamine (the monoamine preferably as a solvent for the triazene), and, in addition, an aromatic amino azo compound in varying amounts depending on the reactivity of the monoamine, and very small amounts of amino diaryl compounds such as aminobiphenyl, a diaryl amine such as diphenylamine, water, and nitric acid. The nitric acid content typically is no greater than about 0.2 percent of the total weight of the solution, and this generally is insufficient to catalyze the rearrangement of the triazene at a practical rate. In a typical case, the binuclear by-product content is about 0.1 percent or less of the total weight of the solution; and, when the monoamine is aniline, the amount of the triazene rearrangement product, i.e., the amino azo compound, is about 1–2 percent on the same basis, larger amounts of the amino azo compound being present in the starting material with more reactive monoamines (as shown in Example 7).

The monoamine-containing solution in which the rearrangement is carried out is dilute with respect to triazene concentration. It has been found that the formation of binuclear by-products, including the carcinogenic 4-aminobiphenyl, is suppressed when the concentration of the 1,3-diaryl triazene in the monoamine-containing solution is low. According to the present invention, the concentration of the triazene in this solution is controlled so as not to exceed about 30 percent, based on the weight of the solution. Within a properly chosen set of time-temperature conditions, a triazene concentration of about 30 percent or lower, and preferably in the range of about from 15 to 25 percent, allows the total binuclear by-product content of the rearrangement product solution to be kept safely below 2, and usually well below 1, percent. Generally the triazene concentration will be no lower than about 5 percent because of the unfavorable economics associated with the handling and working-up of a large volume of material containing too low a concentration of the amino azo compound.

If the diazotization-coupling reaction product has too high a triazene concentration to satisfy the above-discussed requirement, more monoamine can be added thereto prior to the rearrangement.

The concentration of the strong acid and the temperature affect the rate at which the triazene rearranges, and the rate-dependent contact time at a given temperature (also dependent on the triazene concentration) in turn affects the binuclear by-product content of the rearrangement product solution. Higher acid concentrations and higher temperatures result in higher rates of rearrangement. Binuclear formation also is dependent on the temperature used. Within limits, it is desirable to select an acid concentration and temperature that will allow the essentially complete rearrangement of the triazene in as short a time as is practical, not only as an economical measure but also to reduce the chances for binuclear by-product formation. The higher the temperature, the shorter the contact time should be to avoid excessive binuclears. Temperatures above about 120° C. should be avoided in any case, and temperatures not in excess of about 100° C. are preferred to assure the repression of binuclears over a wider range of contact times. As the reaction temperature decreases, the para-/ortho isomer ratio of the aromatic amino azo compound increases, and lower temperatures, e.g., about 90° C. or lower, therefore usually will be especially preferred. Temperatures as low as about 50° C. can be used, however.

The minimum strong acid concentration that can be used depends on the reaction rate attainable therewith to achieve substantially complete rearrangement at a given triazene concentration and temperature. With triazene concentrations and temperatures at the high end of the operable range, substantially complete rearrangement can be achieved at a practical rate when the acid concentration is as low as about 0.4 percent, based on the weight of the triazene-containing solution. Therefore, this is the minimum acid concentration that will be used.

Higher acid concentrations are advantageous in that they cause an increase in the reaction rate. Acid concentrations above about 2.0 percent generally will not be employed owing to the costs involved in disposing of large quantities of salts formed when the acidic rearrangement product solution is neutralized. Considering both the reaction rate and waste disposal factors, acid concentrations in the range of about from 0.7 to 1.3 percent are preferred.

Various strong acids can be used in the present process, some more preferred than others. Mineral acids are preferred, and, of these, nitric acid is especially preferred because it is already present in low concentrations in the reaction solution obtained by diazotizing-coupling a monoamine by means of nitrogen oxide-containing gases. Halogen acids, with the exception of hydriodic acid, can be used but tend to cause larger amounts of binuclear by-products to be produced. Other strong acids that are useful include tetrafluoroboric acid, (trifluoromethyl)acetic acid, fluorosulfonic acid, and strong acid ion-exchange resins.

The purity of the monoamine used in the rearrangement process as well as in the preceding diazotization-coupling can have an effect on the extent of binuclear by-product formation. Alicyclic ketones, e.g., cyclohexanone, and their monoamine Schiff bases, e.g., the aniline-cyclohexanone Schiff base, if present in the monoamine, can be promoters of binuclear by-product formation.

As is described in U.S. Pat. No. 4,020,052, on the basis of minimizing side-reactions, preferred $NO_2$—NO mixtures for the diazotization-coupling reaction are mixtures ranging from about 40/60 to 60/40 $NO_2$/NO by volume.

The invention is illustrated by the following examples.

EXAMPLE 1

The method of the invention was carried out in a continuous manner as follows:

I. Preparation of 1,3-diphenyltriazene (according to U.S. Pat. No. 4,020,052
   a. Synthesis of nitrogen oxide-containing gas mixture Nitric oxide and air were fed into a pipeline reactor at 79 psig (648 kPa) at rates of 0.12 and 0.13 standard cubic feet per minute ($0.57 \times 10^{-4}$ and $0.61 \times 10^{-4}$ m$^3$/s), respectively, with a hold-up time sufficient to allow the reaction of 95–97% of the oxygen fed and to produce a gas mixture containing equal volumes of nitrogen dioxide and nitric oxide. Heated nitrogen was added to the product gas at a rate of 0.82 standard cubic feet per minute ($0.39 \times 10^{-3}$ m$^3$/s) to give a final stream containing 10.8 mole percent nitrogen oxides at a temperature of 74° C., and less than 0.14 mole percent residual oxygen. This gas mixture, except for water, simulated that which would be produced by burning 12.3% ammonia in air of 80% relative humidity at 30° C.

b. Reaction of nitrogen oxides with aniline

Aniline and water (the latter in the amount which would be present in the ammonia oxidation process gas described in Paragraph (a)) were added, at rates of 108 grams/minute and 4.3 milliliters/minute, respectively, through a water-cooled condenser and thence into a vapor-liquid separator designed for continuous drawoff. The reaction product solution (1,3-diphenyltriazene dissolved in aniline) and gases produced in a tubular reactor also passed into the separator liquid being withdrawn from the separator continuously to maintain a constant level. Part of the withdrawn liquid was recovered, and part of it was recirculated through a cooler to maintain a temperature of 40°–50° C., and then to the tubular reactor at a rate of about 2300 milliliters per minute.

The nitrogen oxide-containing gas stream produced as described in Paragraph (a) was passed through the reactor concurrently with the recirculated aniline solution stream, and the product (liquid and gas) passed into the separator as described above.

Analysis of the liquid recovered from the separator indicated the following composition, by weight:
1,3-Diphenyltriazene—19.3%
Aniline—78.0%
p-Aminoazobenzene—1.3%
o-Aminoazobenzene—0.05%
Aminobiphenyls—0.022%
Nitric acid—0.12%
Water—1.00%

II. Rearrangement of 1,3-diphenyltriazene

The above-described essentially homogeneous triazene-containing reaction solution obtained by the diazotization-coupling of aniline as described in Part I (above) was allowed to flow at a rate of 112 milliliters per minute through a 6-foot (1.8 meter)-long, 0.43-inch (1.09-cm)-inner diameter preheater tube, the first 12 inches (0.34 m) of which was packed with fine wire mesh so as to constitute a mixing zone. The temperature in the preheater tube was 40° C. At the same time, a 20 percent by weight solution of nitric acid was introduced into the mixing zone of the preheater tube at a rate of 3.6 milliliters/minute. The total amount of nitric acid contacted with the aniline solution was 0.9 percent of the weight of the solution. The mixture leaving the preheater flowed through 40 feet (12 meters) of 0.5-inch (1.3-cm)-outer-diameter stainless steel tubing (0.43-inch (1.09-cm) inner diameter) at a rate of 116 milliliters/minute, providing a hold-up time in the reactor tubing of 10 minutes (1145 cc reactor volume). Hot water was circulated through a jacket around the reactor tubing to maintain a reaction temperature of 85° C., as indicated at the reactor exit.

Samples were withdrawn periodically at the reactor exit and analyzed. The effluent had the following composition, by weight:
p-Aminoazobenzene—18.7%
o-Aminoazobenzene—2.06%
Aniline—75.3%
1,3-Diphenyltriazine—0%
Aminobiphenyls—0.101%
Diphenylamine—0.026%

The reactor effluent, provided an aniline solution that could be used as the starting material for converting p-aminoazobenzene to p-phenylenediamine, or a solution from which the aminoazobenzene could be recovered.

EXAMPLE 2

Aniline (132.4 grams) at room temperature was charged to a 150-milliliter glass reactor equipped with an outer condenser sleeve, two heated sidearm capillary gas inlet tubes (near the bottom of the reactor), a thermocouple, and a 150 millimeter-long water-cooled condenser.

A gas mixture having the composition 6.7% $NO_2$, 4.3% NO, 17% water vapor, and 72% nitrogen at an average temperature of 200° C. (175°–225° C.) and a pressure of 101 kPa was fed into the room temperature aniline via one of the heated gas inlet tubes at a rate of 290 milliliters per minute. This mixture simulated a gas which had been produced by the oxidation of ammonia according to known processes. During the addition of the gas, the aniline was stirred at about 1000 revolutions per minute. The bulk temperature rose to 45°–50° C. and was maintained there by air-cooling.

The gas flow was stopped after 180 minutes. The reaction liquid, which was substantially homogeneous at the reaction temperature, was cooled to 25° C., whereupon an aqueous layer and an organic layer separated out. The weight of the organic layer was 133.2 grams. The composition of the organic layer was:

| Compound | Wt.-% |
| --- | --- |
| 1,3-diphenyltriazene | 19.8 |
| p-aminoazobenzene | 1.63 |
| o-aminoazobenzene | 0.12 |
| aminobiphenyls | 0.18 |
| p- and o-nitroanilines | 0.04 |
| water | 1.87 |
| nitric acid | 0.09 |
| aniline + water | balance |

A solution (2.8 milliliters) containing (by weight) 13.8% nitric acid, 70.3% aniline, and 15.9% water was added to 53.9 grams of the above triazene solution at 50° C. The concentration of the nitric acid in the combined solutions was 0.85 wt %. The solution was heated up to 90° C. in approximately 3 minutes, and maintained at this temperature for an additional 27 minutes. Heating was discontinued, 25 ml of 25% sodium hydroxide was added, and the neutralized mixture stirred for 1 minute. After removal of an aqueous layer, the organic layer was found to have the following composition:

| Compound | Wt.-% |
| --- | --- |
| p-aminoazobenzene | 19.6 |
| o-aminoazobenzene | 2.76 |
| 2-aminobiphenyl | 0.33 |
| 3-aminobiphenyl | 0.02 |
| 4-aminobiphenyl | 0.08 |
| diphenylamine | 0.08 |
| p- and o-nitroanilines | 0.04 |
| aniline + water | balance |

EXAMPLE 3

A diazotized mixture of aniline was prepared as described in Example 1 with the exception that $NO_2$ was 40 percent of the $NO_2$—NO mixture. The composition of the organic layer obtained after separation of an aqueous layer as described in Example 2 was:

| Compound | Wt-% |
| --- | --- |
| 1,3-diphenyltriazene | 25.1 |
| p-aminoazobenzene | 6.07 |
| o-aminoazobenzene | 0.48 |
| aminobiphenyls | 0.20 |
| o- and p-nitroanilines | 0.32 |
| aniline + water | balance |

The effect of the concentration of 1,3-diphenyltriazene (i.e., conversion to 1,3-diphenyltriazene) on the amount of binuclear by-products formed was determined by appropriate dilution of the above neutralized mixture with aniline followed by rearrangement at 90° C. with 1% nitric acid. The results of these rearrangements as a function of the composition of the initial diazotization solution are shown in Table I.

TABLE I

| Composition of Diazotized Product (Wt-%) | | | | | |
| --- | --- | --- | --- | --- | --- |
| 1,3-diphenyltriazene | 25.1 | 20.8 | 17.0 | 12.4 | 4.04 |
| p-aminoazobenzene | 6.07 | 4.98 | 4.05 | 3.11 | 1.03 |
| o-aminoazobenzene | 0.48 | 0.35 | 0.35 | 0.19 | 0.06 |
| aminobiphenyls | 0.20 | 0.15 | 0.15 | 0.098 | 0.04 |
| o- and p-nitroanilines | 0.32 | 0.36 | 0.28 | 0.12 | 0.029 |

TABLE I-continued

| Composition of Rearranged Product (Wt-%) | | | | | |
|---|---|---|---|---|---|
| p-aminoazobenzene | 25.7 | 20.3 | 17.8 | 14.1 | 4.81 |
| o-aminoazobenzene | 3.01 | 2.30 | 2.00 | 1.59 | 0.61 |
| 2-aminobiphenyl | 0.454 | 0.330 | 0.243 | 0.164 | 0.036 |
| 3-aminobiphenyl | 0.017 | 0.014 | 0.011 | 0.005 | trace |
| 4-aminobiphenyl | 0.087 | 0.076 | 0.051 | 0.033 | trace |
| diphenylamine | 0.197 | 0.110 | 0.083 | 0.017 | trace |

EXAMPLE 4

A diazotized mixture of aniline was prepared as described in Example 1. The $NO_2$ content of the $NO_2$—NO mixture was 45%. The composition of the organic layer was:

| Compound | Wt-% |
|---|---|
| 1,3-diphenyltriazene | 18.3 |
| p-aminoazobenzene | 1.34 |
| o-aminoazobenzene | 0.081 |
| aminobiphenyls | 0.080 |
| nitric acid | 0.20 |
| p- and o-nitroanilines | 0.079 |
| aniline + water | 79.9 |

The rearrangement of this mixture was carried out in the manner described in Example 2. The concentration of nitric acid was 1 wt-%. The effect of the rearrangement temperature is summarized in Table II.

TABLE II

| Compound | 75° C. | 90° C. | 115° C.* |
|---|---|---|---|
| | Wt-% | | |
| p-aminoazobenzene | 16.8 | 17.9 | 17.2 |
| o-aminoazobenzene | 1.67 | 1.95 | 2.11 |
| 2-aminobiphenyl | 0.112 | 0.108 | |
| 3-aminobiphenyl | 0.012 | 0.010 | 0.220 |
| 4-aminobiphenyl | 0.029 | 0.028 | |
| Diphenylamine | 0.026 | 0.023 | |
| Ratio p/o aminoazobenzene | 10.0 | 9.2 | 8.1 |

*neutralized mixture

EXAMPLE 5

A diazotized mixture of aniline was prepared in the manner described in Example 1 with the exception that water was absent from the nitrogen oxide mixture and the $NO_2$ content of the $NO_2$—NO mixture was 45%. The organic layer had the following composition:

| Compound | Wt-% |
|---|---|
| 1,3-diphenyltriazene | 17.5 |
| p-aminoazobenzene | 2.34 |
| o-aminoazobenzene | 0.187 |
| aminobiphenyls | 0.095 |
| p- and o-nitroanilines | 0.048 |
| nitric acid | 0.22 |
| aniline + water | 79.6 |

Rearrangement of this mixture was performed in the manner described in Example 2. The concentration of nitric acid and the rearrangement temperature were varied to show their effect on the amount of binuclear by-products as well as the p/o aminoazobenzene ratio. The results are summarized in Table III.

It is seen that more binuclear by-products are obtained at the lower acid concentration for all the temperatures, whereas only small changes are observed at nitric acid concentrations of 1.0 to 1.8 wt %. It can also be seen that the para to ortho ratio is higher at 50° C. than at 90° C.

TABLE III

| Conditions | | | | | | | | | |
|---|---|---|---|---|---|---|---|---|---|
| T, °C. | 50 | 50 | 50 | 75 | 75 | 75 | 90 | 90 | 90 |
| Wt-% $HNO_3$ | 0.61 | 1.0 | 1.78 | 0.61 | 1.0 | 1.78 | 0.61 | 1.0 | 1.78 |
| Products | Wt-% | | | | | | | | |
| p-aminoazobenzene | 19.0 | 18.1 | 18.4 | 19.0 | 18.6 | 18.1 | 16.8 | 17.6 | 17.3 |
| o-aminoazobenzene | 1.59 | 1.65 | 1.52 | 2.08 | 1.83 | 1.92 | 1.95 | 1.96 | 1.81 |
| 2-aminobiphenyl | 0.095 | 0.077 | 0.070 | 0.106 | 0.070 | 0.072 | 0.106 | 0.077 | 0.072 |
| 3-aminobiphenyl | trace | trace | 0.009 | trace | trace | trace | 0.004 | 0.005 | trace |
| 4-aminobiphenyl | 0.023 | 0.018 | 0.018 | 0.028 | 0.021 | 0.022 | 0.043 | 0.022 | 0.021 |
| diphenylamine | 0.023 | 0.013 | 0.014 | 0.025 | 0.018 | 0.015 | 0.063 | 0.016 | 0.014 |
| p/o-aminoazobenzene ratio | 11.9 | 11.0 | 12.1 | 9.1 | 10.2 | 9.4 | 8.6 | 9.0 | 9.6 |

EXAMPLE 6

A diazotized mixture of aniline was prepared in the manner described in Example 1 with the exception that the % $NO_2$ of the $NO_2$—NO mixture was varied between 40% and 60%. These gas compositions were obtained by varying the hold-up time in the oxidation of NO to $NO_2$ to provide the proper ratio of NO to $NO_2$ in the feed.

The diazotized mixtures had the following compositions:

| % $NO_2$ | 40 | 50 | 60 |
|---|---|---|---|
| Product | Wt-% | | |
| 1,3-diphenyltriazene | 17.3 | 18.7 | 16.7 |
| p-aminoazobenzene | 2.00 | 2.37 | 2.83 |
| o-aminoazobenzene | trace | 0.14 | 0.023 |
| aminobiphenyls | 0.040 | 0.091 | 0.129 |
| nitric acid | 0.16 | 0.28 | 0.36 |
| aniline + water | 80.4 | 78.2 | 79.6 |
| p- and o-nitroanilines | 0.092 | 0.215 | 0.319 |

Rearrangement of these mixtures at 90° C. was performed in the manner described in Example 2. The concentration of the nitric acid employed was 1%. The results of these rearrangements as a function of the % $NO_2$ of the $NO_2$—NO component of the feed gas are summarized in Table IV.

TABLE IV

| % NO$_2$ of the NO$_2$—NO Component in Feed | 40 | 50 | 60 |
|---|---|---|---|
| Product | | Wt-% | |
| p-aminoazobenzene | 18.9 | 18.3 | 18.8 |
| o-aminoazobenzene | 2.11 | 2.24 | 2.17 |
| 2-aminobiphenyl | 0.106 | 0.166 | 0.196 |
| 3-aminobiphenyl | 0.003 | 0.015 | 0.008 |
| 4-aminobiphenyl | 0.025 | 0.037 | 0.044 |
| diphenylamine | 0.025 | 0.033 | 0.041 |
| aniline + water | balance | balance | balance |

It is seen from Table IV that the amount of binuclear by-products is higher for the diazotized mixtures obtained from the higher % NO$_2$ of the NO$_2$—NO component.

EXAMPLE 7

The procedure described in Part I of Example 1 was repeated with the exception that o-toluidine was substituted for the aniline. The reaction of o-toluidine with the nitrogen oxides was effected at 45° C., whereby 23.5% of the o-toluidine was converted to a mixture of 55% 1,3-di-o-tolyltriazine and 45% dimethyl aminoazobenzenes.

The triazene-containing reaction solution was treated in the same way as that described in Part II of Example 1, except that a reaction temperature of 55° C. was maintained.

The reactor effluent had the following composition, by weight:

3,2'-Dimethyl-4-aminoazobenzene—22.4%
3,2'-Dimethyl-2-aminoazobenzene—0.86%
Binuclears—0.069%
o-Toluidine—73.7%

The reactor effluent, provided an o-toluidine solution that could be used as the starting material for converting 3,2'-dimethyl-4-aminoazobenzene to 2-methyl-p-phenylenediamine.

I claim:

1. A method of preparing a carbocyclic aromatic amino azo compound with a high para/ortho isomer ratio and minimum formation of binuclear byproducts comprising contacting a strong acid at a temperature in the range of about from 50° C. to 120° C. with a solution separated from the gas/liquid product obtained by the treatment of an excess of a primary carbocyclic aromatic monoamine with a gas containing nitric oxide and nitrogen dioxide to effect the diazotization-coupling of said monoamine, said solution being substantially homogeneous at said temperature and containing said primary carbocyclic aromatic monoamine and up to about 30 percent by weight of a dissolved 1,3-diaryl triazene based on the weight of said solution, and the weight of said strong acid being about from 0.4 to 2.0 percent of the weight of said triazene-containing solution contacted therewith.

2. A method of claim 1 wherein said 1,3-diaryl triazene is dissolved in primary carbocyclic aromatic monoamine that has been unconsumed in the diazotization-coupling reaction.

3. A method of claim 2 wherein said strong acid is contacted with a solution separated from the gas/liquid product obtained by the treatment of an excess of said monoamine with a gas mixture derived from the oxidation of ammonia.

4. A method of claim 1 wherein said strong acid is nitric acid.

5. A method of claim 1 wherein said monoamine is aniline or o- or m-toluidine, and said triazene is 1,3-diphenyltriazene or 1,3-di-o- or 1,3-di-m-tolyltriazene, respectively.

6. A method of claim 3 wherein said strong acid is nitric acid and is contacted with said solution directly after the separation of said solution from the gas/liquid product obtained by the treatment of said monoamine with said gas mixture.

7. A method of any one of claims 1 through 6 wherein said solution contains a maximum of about 0.1 percent of binuclear by-products from the diazotization-coupling reaction.

8. A method of claim 3, 4 or 5 wherein said temperature is about 90° C. or less, said solution contains about from 15 to 25 percent by weight of said triazene, and the weight of said strong acid is about from 0.7 to 1.3 percent of the weight of said solution.

9. A method of preparing aminoazobenzene with a high para/ortho isomer ratio and minimum formation of binuclear by-products comprising contacting nitric acid at a temperature of about from 50° C. to 90° C. with a solution separated from the gas/liquid product obtained by the treatment of excess aniline with a gas containing nitric oxide and nitrogen dioxide to effect the diazotization-coupling of said aniline, said solution being substantially homogeneous at said temperature and containing about from 15 to 25 percent by weight, based on the weight of said solution, of 1,3-diphenyltriazine dissolved in aniline that has been unconsumed in the diazotization-coupling reaction, and the weight of said nitric acid being about from 0.7 to 1.3 percent of the weight of said solution.

10. A method of claim 1 or 9 wherein about from 40 to 60 percent of said gas containing nitric oxide and nitrogen dioxide is nitrogen dioxide, based on the total volume of said oxides.

* * * * *

UNITED STATES PATENT AND TRADEMARK OFFICE
CERTIFICATE OF CORRECTION

PATENT NO. : 4,279,815
DATED : July 21, 1981
INVENTOR(S) : Frank E. Herkes

It is certified that error appears in the above—identified patent and that said Letters Patent is hereby corrected as shown below:

On the title page, Item [73] should be added to read:

--- E. I. du Pont de Nemours and Company, Wilmington, Del. ---.

Signed and Sealed this

First Day of December 1981

[SEAL]

Attest:

Attesting Officer

GERALD J. MOSSINGHOFF

Commissioner of Patents and Trademarks